United States Patent [19]
Arnold et al.

[11] Patent Number: 5,135,758
[45] Date of Patent: Aug. 4, 1992

[54] PROCESS FOR COMBATTING "VARROATOSIS" BY BIOLOGICAL MEANS AND DEVICES FOR IMPLEMENTING THIS PROCESS

[75] Inventors: Gérard Arnold, Rambouillet; Claudine Masson, Orsay; Yves Le Conte, Orleans; Jérôme Trouiller, Paris; Bertrand Chappe, St Remy les Chevreuse; Guy Ourisson, Strasbourg, all of France

[73] Assignees: Institute National de la Recherche Agronomique (INRA); Centre National de la Recherche Scientifique (CNRS), both of Paris, France

[21] Appl. No.: 499,500
[22] PCT Filed: Oct. 31, 1989
[86] PCT No.: PCT/FR89/00565
§ 371 Date: Aug. 28, 1990
§ 102(e) Date: Aug. 28, 1990
[87] PCT Pub. No.: WO90/04922
PCT Pub. Date: May 17, 1990

[30] Foreign Application Priority Data
Nov. 3, 1988 [FR] France .................. 88 14349

[51] Int. Cl.[5] .................. A01N 63/02; A01N 37/02; A01N 37/06
[52] U.S. Cl. .................. 424/539; 424/84; 514/532; 514/552
[58] Field of Search .................. 424/539, 84; 514/532, 514/552

[56] References Cited
U.S. PATENT DOCUMENTS
4,299,816 11/1981 Polyakov et al. .................. 514/490
4,965,287 10/1990 Stendel et al. .................. 514/531

Primary Examiner—Richard L. Raymond
Assistant Examiner—S. Mark Clardy
Attorney, Agent, or Firm—Fleit, Jacobson, Cohn, Price, Holman & Stern

[57] ABSTRACT

This process for combatting *Varroa jacobsoni* by biological means, an ectoparasitic acarian specific to the genus Apis, is characterized in that there is introduced, into the environment in which said acarian may be present, an attractant product consisting of a total hexane extract of bee larvae; or of an active fraction of such an extract; or of at least one active ester derived from a $C_1$–$C_6$ aliphatic alcohol and from a $C_{10}$–$C_{24}$ carboxylic acid; or of a mixture of methyl and ethyl palmitates, stearates, oleates, linoleates and linolenates, or an active mixture of at least two of these esters; or ethyl palmitate, methyl palmitate, methyl linolenate or mixtures thereof, optionally with another ester.

27 Claims, 3 Drawing Sheets

PROCESS FOR COMBATTING "VARROATOSIS" BY BIOLOGICAL MEANS AND DEVICES FOR IMPLEMENTING THIS PROCESS

The present invention relates to a process for combatting, by biological means, varroatosis, a serious parasitosis of bees which is due to *Varroa jacobsoni* Oud., an ectoparasitic acarian specific to the genus Apis. This biological combatting process comprises two aspects: first, that of the diagnosis of this parasitosis, and, in the case where it is present, the trapping and destruction of the acarian. The present invention also relates to trapping devices for implementing this process.

Varroatosis appeared in France in 1982 after being propagated in Asia and in Western Europe. It is also wreaking havoc in Africa and in South America, and has been present for a few months in the USA.

*Varroa jacobsoni* finds, in colonies of the domestic bee *Apis mellifica*, the optimal climatic and trophic conditions it requires for its development. By drawing out the hemolymph from the workers and males—in the adults as well as in the larvae and pupae—it causes considerable problems in these insects, generally leading to their early death. The bee colony is hence greatly weakened, and it disappears after approximately 4 years. In addition, the parasitized colonies are rapidly contaminated by secondary infections, especially viral infections, which further accelerate their extinction.

By way of example, a survey carried out by the Syndicat des Producteurs de Miel (Union of Honey Producers) of France at the end of 1986 revealed that, in the Mediterranean region, all the colonies were parasitized, and that a large proportion of them were in a critical situation.

The disappearance, or even the weakening, of colonies has considerable negative consequences from both the agronomic and the ecological standpoint:

The disappearance of bee colonies leads to a decrease in the pollination of many cultivated plants, the bee being the main pollinating insect. The negative effects on some plant productions are considerable in large-scale growing, in hybrid seed production, in arboriculture and in small-fruit crops. Also, the disappearance of bee colonies leads to a lower profitability of beekeeping enterprises as a result of the losses of colonies, the decrease in honey collected and the extra costs of production due to chemical treatments. From the ecological standpoint, bees participate in a general way in the ecological balance by pollinating many wild plants, and their disappearance runs the risk of upsetting this balance.

The only treatments presently effective against *Varroa jacobsoni* are chemical treatments based on acaricidal molecules. However, the use of these products has various drawbacks: on the one hand the acarians become more or less rapidly resistant to these molecules, and on the other hand they run the risk of sullying the image of the healthy and natural products of the hive, and especially honey. Although no trace of residue has ever been detected in France, it is not possible to foresee the future regarding this matter. In addition, the method of use of these molecules can have some drawbacks: if their duration of action is short (from a few hours to a few days), the many varroas which are inside the capped cells are not reached by the molecules and will emerge a few days later to reproduce in their turn and prolong the infestation; such methods are hence of limited efficacy. Conversely, if their duration of action is long (a few weeks), the molecules can pass into the wax or the honey after a certain period of time and contaminate them. In addition, the use of acaricides for long periods is not without risks of toxicity to the bees themselves.

It is observed that, in order to reproduce, the female *Varroa jacobsoni* leaves the adult bee and enters a cell containing a worker larva or male larva, with a preference for male larvae, approximately two days before capping. The Applicants have then been able to demonstrate the existence of kairomones emitted by *Apis mellifica* ligustica larvae which have an attractive effect on the *Varroa jacobsoni* under the temperature conditions of the colony. The active principles of these kairomones are at the heart of the biological combatting process which forms the subject of the present invention, and whose development has become urgent in view of the fact that, as stated above, this acarian currently represents, at international level, the most serious danger threatening *Apis mellifica* bee colonies.

The present invention hence relates, first, to a process for combatting *Varroa jacobsoni* by biological means, characterized in that there is introduced, into the environment in which said acarian may be present, an attractant product consisting of:

a total hexane extract of bee larvae, in particular of male larvae and worker larvae, especially of larvae of males (drones), these larvae being, in particular, larvae of *Apis mellifica* ligustica bees;

an active fraction (that is to say a fraction responsible for the attraction of *Varroa jacobsoni*) of a total hexane extract of bee larvae, this fraction resulting, in particular, from a fractionation on a silica column of the abovementioned total hexane extract;

at least one active ester derived from a $C_1$–$C_6$ aliphatic alcohol such as methanol and ethanol and from a straight- or branched-chain $C_{10}$–$C_{24}$ carboxylic acid, saturated or comprising one or more conjugated or unconjugated, cis or trans double bonds, it being possible for a benzene ring or a heterocycle to be included in the chain of said acid;

a product consisting of a mixture of:
 methyl palmitate,
 ethyl palmitate,
 methyl stearate,
 ethyl stearate,
 methyl oleate,
 ethyl oleate,
 methyl linoleate,
 ethyl linoleate,
 methyl linolenate,
 ethyl linolenate; or alternatively of an active mixture of at least two of these esters;

methyl palmitate, ethyl palmitate, methyl linolenate or a mixture of two of these esters or a mixture of all three, or alternatively a mixture containing at least one of these esters with at least one other ester not in itself having attractant activity;

a mixture of esters of the type defined above, and obtained by transesterification from an oil, such as groundnut oil or sunflower oil.

Figure 1:
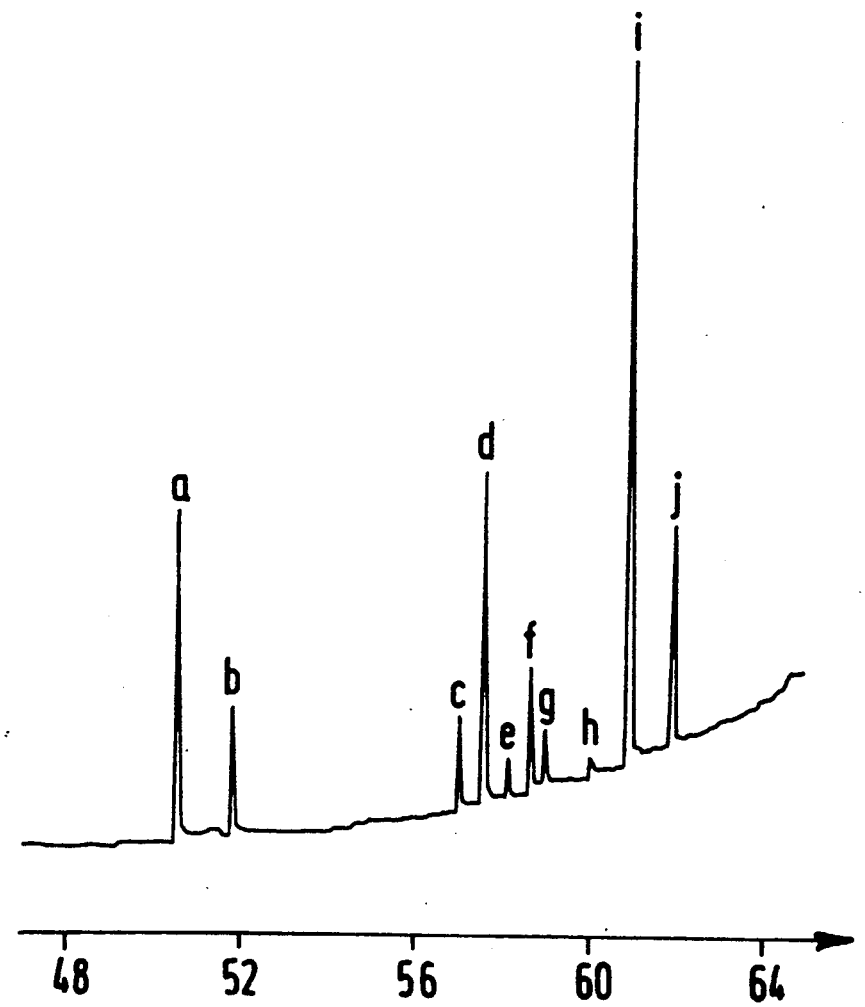
FIG. 1 shows the GC chromatogram of the male bee larvae extract.

According to a preferred embodiment of this process, the attractant product is introduced into the environment in which the *Varroa jacobsoni* acarian may be present at a temperature of between 30° and 36° C.

It is also possible to combine the attractant product with at least one adjuvant designed to increase its volatility, this adjuvant being selected, in particular, from organic esters more volatile than those mentioned above and not having the attractant activity according to the invention.

Combination with such an adjuvant enables this biological combatting process to be applied at temperatures below 30° C., which can prevail, depending on the season, in the hive, especially in the bottom of the hive, which is the most readily accessible part for arranging the trap according to the invention, as will be described below.

It is also possible to vary the rate of volatilization of the attractant product by solubilizing the latter in an organic substance, such as a paraffin, a vegetable wax or beeswax; by placing it in the form of a colloidal suspension in water, immobilized or otherwise by a gelling agent; or alternatively by including it in a solid vehicle, such as infusorial earth.

Also, it is possible to arrange to combine the attractant product with at least one hormone, such as a juvenile hormone, as well as at least one inert solid diluent, such as infusorial earth, alumina, cellulose or a modified cellulose, polyoxyethylene, dry vegetable matter or polymers, such as polyethylene or polyvinyl chloride.

It is also possible to envisage applying the attractant product by spraying or vaporization (aerosol).

In the case where the aim is to trap the acarian, the attractant product can either be combined with a means for trapping the acarian by agglutination; or with a contact pesticide or acaricide, in particular one having little or no volatility, thereby destroying the acarian, or alternatively a sterilizing agent, thereby preventing it from proliferating.

In a preferred embodiment, the attractant product is applied in the hive, at the entrance to the hive or outside of the hive, within a trap, preventing if necessary, by means of a protective grid, the bees from entering said trap.

Depending on the temperature of the colony (which varies, in particular, with the season and the presence of brood comb), and depending on the location in which the trap is placed (in, at the entrance to or outside of the hive), this process is advantageously combined with a heat treatment so as to increase its efficacy. It has, in effect, been noted that methyl palmitate, in particular, is very active at 34° C. but is no longer active at 22° C.; in point of fact, 34° C. happens to be the average temperature of bees' brood comb. For this molecule in particular, it is hence of interest to note that the temperature appropriate to its efficacy is slightly above its melting point (28°–30° C.).

Thus, the biological control process according to the invention has two complementary aspects:
on the one hand, it may be used as a process for diagnosis of the parasitosis (warning method): the beekeeper will thus be informed of the presence of the parasite and of the extent of the infestation, and hence, where appropriate, to undertake a controlled application of an acaricidal treatment;

on the other hand, it may be used as an actual control process, the acarians being removed by means of traps (the active molecules being used in chemical lures), being simply trapped, for example by an adhesive substance, or killed, for example, by a contact acaricide.

Thus, the present invention also relates to a device for implementing the process as has just been described, this device being characterized in that it consists of a trap capable of attracting the *Varroa jacobsoni* acarian by the presence of the attractant product as defined above, optionally combined with at least one adjuvant designed to increase its volatility and/or to vary its rate of volatilization, and/or with at least one inert diluent and/or with at least one hormone.

In a particular embodiment, the trap comprises a support carrying an adhesive coating in which a quantity of attractant product and, where appropriate, of a pesticide, an acaricide and/or a sterilizing agent is incorporated, or alternatively a porous support impregnated with a quantity of attractant product and, where appropriate, of pesticide, acaricide and/or sterilizing agent. In particular, it is possible to use an elongated support which is arranged flat on the floor of the hive, in the center of the latter.

In another particular embodiment, the trap consists of an open housing containing the attractant product, where appropriate combined with at least one adjuvant as defined above, and/or with at least one pesticide, an acaricide and/or a sterilizing agent, it being possible for the opening of said housing to be closed by a grid preventing the bees from entering said housing. Thus, in the case of an addition of a contact acaricide (for example, in cases of very heavy infestation), it would no longer need to be feared that this acaricide might pollute the colony since, on the one hand the bees would have no contact with this product (presence of the protective grid); and on the other hand the acaricide would not be diffused into the hive in the form of an aerosol, as occurs in some currently authorized methods, and hence not reach the combs where the material to be collected is stored.

The devices according to the invention may also be combined with a means of heating, such as a heating resistor so as to increase the efficacy of the process.

Thus, the main advantage of the process according to the invention is to use molecules which are generally present naturally in the bee colony, and which hence do not run the risk of polluting the various products of the hive: honey, pollen, royal jelly, propolis, wax. It is a process which is easy to use and is suited both to professional beekeepers and to amateurs.

The isolation and identification of the active substances of the invention, followed by the attraction behavior of *Varroa jacobsoni* induced by compounds extracted from bee larvae, will now be described.

I—Isolation and identification of the active substances (a) Extraction

Male larvae of *Apis mellifica ligustica* bees were removed two days before the capping of their cells. Three hundred larvae were extracted in 50 ml of hexane for one hour at room temperature (6 larval equivalents (Eql) per ml).

(b) Column chromatograghy 8 ml of hexane extract (48 Eql) were evaporated and chromatographed on a column of SDS silica (70–230 mesh) 20 cm long, 0.5 cm in diameter. The silica column was washed copiously with ethyl acetate and restabilized with hexane. The extract was eluted successively with 4 ml of hexane (fraction F1), 4 ml of dichloromethane (F2) and 4 ml of ethyl acetate (F3). The active fraction F2 (see section II) was evaporated under a stream of nitrogen and taken up in 2.7 ml of hexane. This hexane solution is analyzed in GC.

(c) Gas chromatograghy

The GC analysis was performed on a Carlo Erba 6000 chromatograph equipped with an on-column injector, an FID detector and an integrator.

Two types of capillary column were used for the analysis of this active fraction:

grafted OV1 (length: 50 m, diameter: 0.32 mm, program: $50°-200°$ C./10° C./min), 200° to 300° C./5° C./min)), carrier gas: hydrogen at $4 \times 10^4$ Pa Carbowax CW20M (length: 50 m; diameter: 0.32 mm. Program: $40°-260°$ C./3° C./min), carrier gas: hydrogen $4 \times 10^4$ Pa.

On the OV1 apolar column, 6 peaks are observed, with shoulders for some peaks. On the CW 20M polar column, a good resolution is obtained and 10 peaks are observed in total.

(d) GC/MS coupling

The GC/MS coupling unit is composed of a Varian 3400 chromatograph equipped with a Split/Splitless injector and a CW 20M column (length: 50 m, diameter: 0.32 mm), helium carrier gas and a Finigan Mat Incos 50 mass spectrometer. The resulting chromatogram is shown in FIG. 1.

(e) Identification

All 10 peaks (a to j) which make up the active fraction F2 were identified and quantified:

| | | |
|---|---|---|
| a) methyl palmitate | 0.26 μg/Eql | |
| b) ethyl palmitate | 0.09 μg/Eql | |
| d) methyl stearate | 0.08 μg/Eql | |
| f) ethyl stearate | 0.04 μg/Eql | |
| c) methyl oleate | 0.07 μg/Eql | |
| e) ethyl oleate | 0.03 μg/Eql | |
| g) methyl linoleate | 0.05 μg/Eql | |
| h) ethyl linoleate | 0.01 μg/Eql | |
| i) methyl linolenate | 0.59 μg/Eql | |
| j) ethyl linolenate | 0.18 μg/Eql | |

Their mass spectra and their retention times in GC on two columns of different polarity are identical with the reference data obtained commercially from Sigma.

II—Study of the attraction behavior of Varroa jacobsoni in the presence of different substances derived from the host insect This study was carried out in a four-option dynamic olfactometer, which permits rigorous control of the flows in the four fields, odorized or otherwise (Vet et al., Physiol. Entomol. 8, pages 97–106 (1983); Kaiser et al., J. Insect. Behav. (1988) (in press). In the protocol selected, in the four fields of the olfactometer, one or two, depending on the case, are odorized, the others being odorless. The device was placed in a thermostatted chamber at $32 \pm 1°$ C. (relative humidity: $90 \pm 5\%$), which is the temperature corresponding to the thermal preference of the acarian (Le Conte and Arnold, Apiidologie, 16(2), pages 155–164 (1988). The distribution of Varroa jacobsoni in the different fields was analyzed according to two complementary methods:

i) A representation in the form of levels of gray of increasing intensity, established by means of a computerized program and corresponding to the cumulative presence of Varroa jacobsoni throughout the period of the experiment (Backchine et al., 1988, in preparation).

ii) The mean number of varroas present in the odorized fields and in the control fields was calculated as a function of the time spent in each field.

Figure 2A:
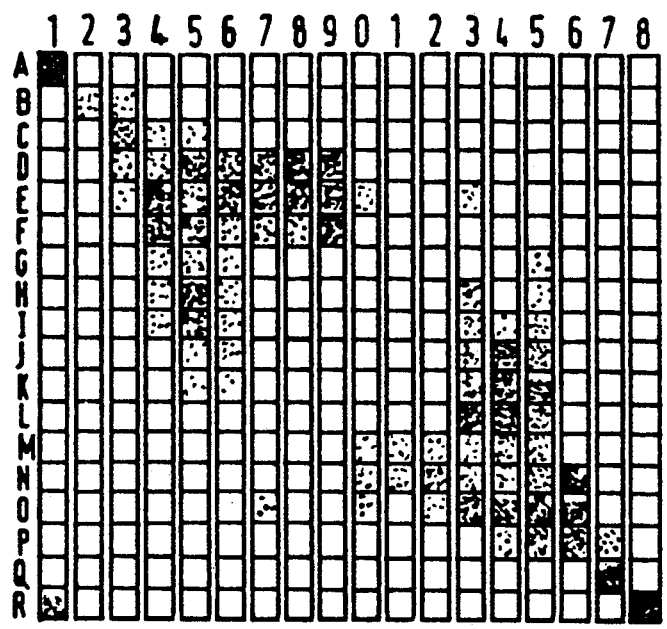
FIG. 2 shows the spatial distribution of the *Varroa jacobsoni* females in the olfactometer.
Figure 2B:
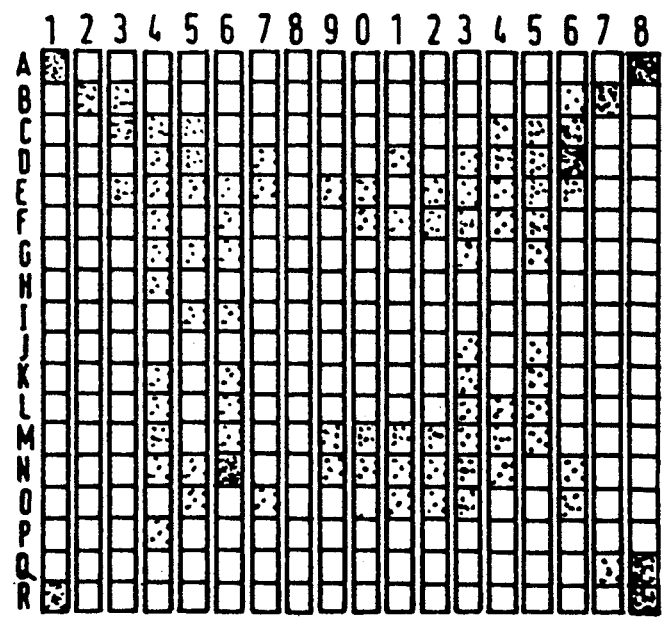

FIG. 2 of the attached drawing shows the spatial distribution of the Varroa jacobsoni females in the olfactometer.

A: Control: the four fields are odorless.

B: Methyl palmitate: two of the four fields (upper left and lower right) are odorized with methyl palmitate; the other two fields are odorless.

Figure 3:
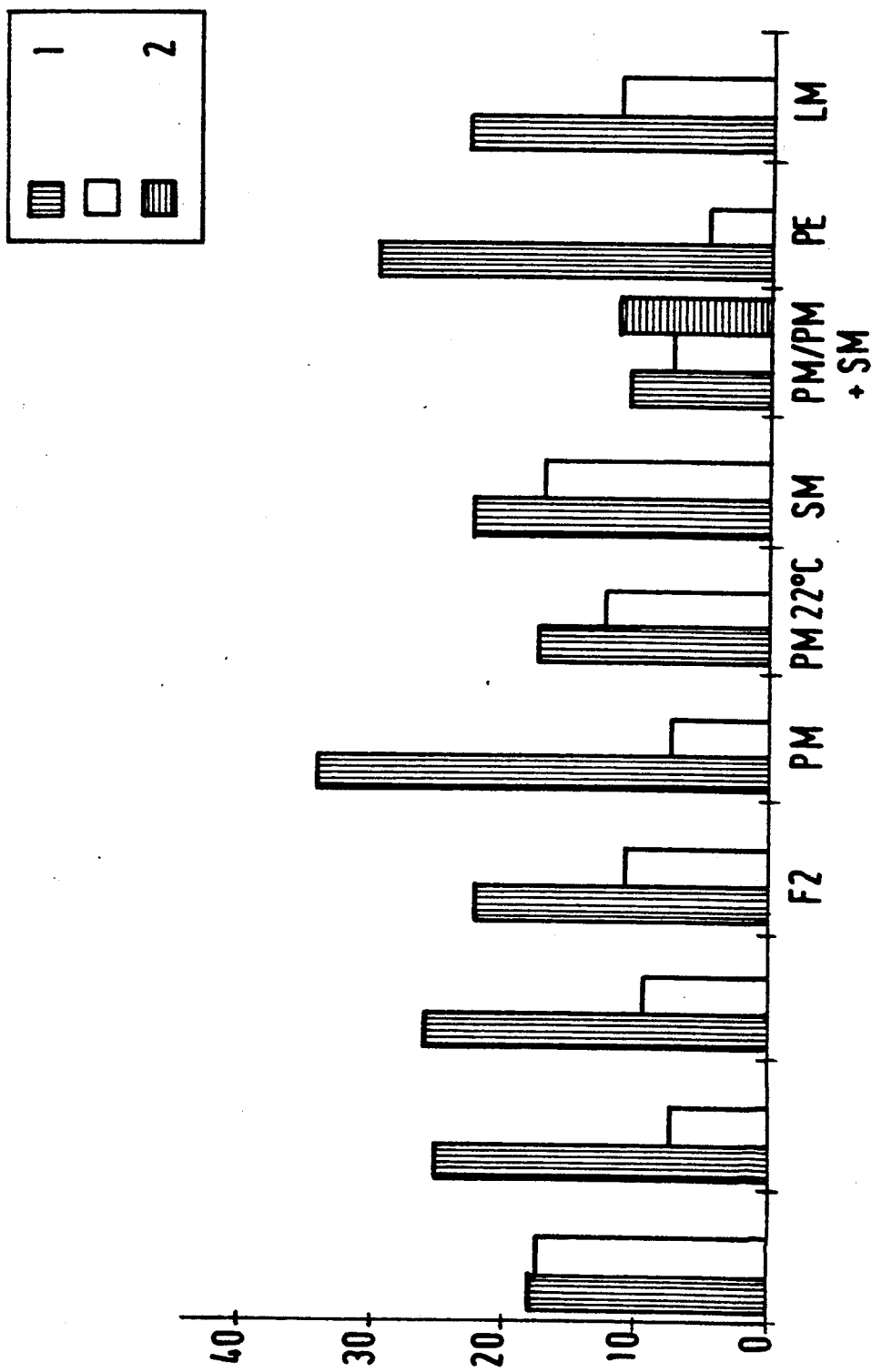
FIG. 3 illustrates the olfactory responses of *Varroa jacobsoni* females to methyl palmitate and to other compounds extracted from male bee larvae.

FIG. 3 illustrates the olfactory responses of Varroa jacobsoni females to methyl palmitate and to other compounds extracted from male bee larvae.

Each of the fields of a four-option dynamic olfactometer was swept with a flow of air at the rate of $0.9 \pm 0.1$ l/h. Depending on the case, one or two of the fields were odorized, the others being odorless. The bee larvae, or the various extracts and compounds whose biological efficacy was to be tested, were arranged in a glass vial connected to one arm of the olfactometer. The extracts were deposited on a $2 \times 2$ cm Whatman filter paper (GF/F); the other vials receiving a control filter paper of the same size. The chemical extracts were renewed in each alternate experiment; beforehand, the olfactometer was cleaned with alcohol and rinsed with distilled water. The device underwent a 90° rotation after 7 consecutive tests in order to eliminate the interference of other signals in the orientation of the acarians.

The varroas used were females taken from a bee colony and maintained at 22° C. for 7 to 9 days on workers in a breeding cage.

56 varroas distributed in two series were used for each test. The acarians were tested individually for 6 minutes 15 seconds. Their position was noted every 5 seconds.

In the absence of odor stimulation, the varroas are distributed at random in the olfactometer (FIG. 2).

The time spent in each of the four fields does not different significantly from the others (Friedman's test, $X^2 = 32.76$; DDL=57) (FIG. 3).

In the presence of 15 live male Apis mellifica ligustica larvae (aged 5 to 6 days), the acarians exhibited a very significant attraction behavior ($X^2 = 7.02$; $p < 0.01$) (FIG. 3), thereby demonstrating that chemical signals are involved in the recognition of the larvae by Varroa jacobsoni females.

A hexane extract of male bee larvae of the same age as those above (representing 1.2 Eql) also proved highly attractant ($X^2 = 7.6$; $p < 0.01$). This extract was fractionated on a silica column in three portions (see section I). Each of the three fractions F1, F2 and F3 (representing 1.8 Eql) was tested by means of the biological test described above; only the fraction F2 proved attractant ($X^2 = 7.28$; $p < 0.01$) (FIG. 3).

The biological efficacy of the molecules identified from the ten compounds present in this fraction was tested on the basis of 1 μg of each constituent per odorized field. Methyl palmitate (MP), ethyl palmitate (EP) and methyl linolenate (ML) separately produced an attraction behavior of *Varroa jacobsoni* identical to that of the total extract (FIG. 3), whereas the other compounds are without effect.

In another trial, a mixture of two molecules, MP and MS (1:1) was tested in competition with MP alone; no significant difference is seen between the two odorized fields ($X^2 = 0.04$). MS hence has no synergistic effect on the attractiveness brought about by MP used alone.

In addition, the attractiveness of MP is closely dependent on the ambient temperature. While at a temperature of $32 \pm 1°$ C. the attraction of MP is highly significant (FIG. 3), when used at a temperature of 22° C., no significant difference in the distribution of the varroas between the fields odorized with MP and the control fields ($X^2 = 0.42$) could be demonstrated (FIG. 3). Heat and chemical factors hence have a synergistic effect on the manifestation of the attraction behavior of *Varroa jacobsoni*. The crucial part played by temperature in the bee-varroa relationships has already been demonstrated (Le Conte and Arnold, 1986, 3rd Meeting of the E. C. Varroa Experts' group, Bad Homburg, West Germany; Le Conte and Arnold, 1987, Apidologie 18(4), pages 305 to 320).

We claim:

1. A process for biologically combatting *Varroa jacobsoni*, an ectoparasitic acarian specific to the genus Apis, which comprises introducing into environment, in which the acarian is or may be present, an attractant effective amount of a product selected from the group consisting of:
   a) a total hexane extract of bee larvae;
   b) an active fraction of a total hexane extract of bee larvae;
   c) at least one active ester derived from a $C_1$-$C_6$ aliphatic alcohol and from a straight- or branched-chain $C_{10}$-$C_{24}$ carboxylic acid optionally comprising a benzene ring or a heterocyclic ring in the chain;
   d) a mixture of methyl palmitate, ethyl palmitate, methyl stearate, ethyl stearate, methyl oleate, ethyl oleate, methyl linoleate, ethyl linoleate, methyl linolenate and ethyl linolenate, or an active mixture of at least two of the enumerated esters; and
   e) an active mixture of esters obtained by oil transesterification.

2. A process of claim 1 wherein the attractant product is a total hexane extract of bee larvae.

3. A process of claim 1 wherein the attractant product is an active fraction of a total hexane extract of bee larvae.

4. A process of claim 1 wherein the attractant product is (a) or (b) and the hexane extract is that derived from male larvae or from worker larvae.

5. A process of claim 1 wherein the attractant product is (b), and the fraction is that resulting from fractionation on a silica column.

6. A process of claim 5 wherein the hexane extract is that derived from male larvae or from worker larvae.

7. A process of claim 1 wherein the attractant product is (c) wherein the carboxylic acid chain is saturated.

8. A process of claim 1 wherein the attractant product is (c) wherein the carboxylic acid chain comprises at least one double bond.

9. A process of claim 1 wherein the attractant product is (c) wherein carboxylic acid chain comprises a benzene ring or a heterocyclic ring.

10. A process of claim 1 wherein the attractant product is (d).

11. A process of claim 10 wherein the attractant product consists of methyl palmitate, ethyl palmitate, methyl linolenate, a mixture of two of these esters or a mixture of all three of these esters.

12. A process of claim 10 wherein the attractant product consists of a combination of at least one ester from each of two groups of esters, the first group consisting of methyl palmitate, ethyl palmitate and methyl linolenate and the second group comprising non-attractant esters.

13. A process of claim 1 wherein the attractant is (e), and the oil is groundnut oil or sunflower oil.

14. A process of claim 1 wherein the attractant product is introduced into the environment at a temperature of between 30° and 36° C.

15. A process of claim 1 wherein the attractant product is in combination with at least one volatility-increasing adjuvant.

16. A process of claim 15 wherein the volatility-increasing adjuvant is an organic ester which is more volatile than (c).

17. A process of claim 1 wherein volatilization of the active product is varied:
   a) by solubilizing said active product in an organic substance;
   b) by colloidally suspending said active product in water with a gelling agent; or
   c) by incorporating said active product in a solid vehicle.

18. A process of claim 17 wherein the organic substance is paraffin, vegetable wax or beeswax, and the solid vehicle is infusorial earth.

19. A process of claim 1 wherein the attractant product is in combination with at least one inert solid diluent.

20. A process of claim 19 wherein the inert solid diluent is infusorial earth, alumina, cellulose, modified cellulose, dry vegetable matter, or polymer.

21. A process of claim 19 wherein the inert solid diluent is polyethylene or polyvinyl chloride.

22. A process of claim 1 wherein the attractant product is in combination with at least one hormone.

23. A process of claim 22 wherein the hormone is a juvenile hormone.

24. A process of claim 1 wherein the attractant product is introduced into the environment by spraying or by vaporization.

25. A process of claim 1 which comprises trapping the acarian by agglutination.

26. A process of claim 1 which comprises combining the attractant with a contact pesticide, with a contact acaricide or with a sterilizing agent and which optionally comprises trapping the acarian.

27. A process of claim 1 wherein the attractant product is applied within a trap located in a hive, at a hive entrance or outside of a hive, the trap optionally having a protective grid to keep bees from entering said trap.

* * * * *